US009066707B2

(12) United States Patent
Dwivedi et al.

(10) Patent No.: US 9,066,707 B2
(45) Date of Patent: Jun. 30, 2015

(54) HEART LOCATION AND VERIFICATION IN EMISSION IMAGES

(75) Inventors: Shekhar Dwivedi, Lucknow (IN); Xiyun Song, Cupertino, CA (US); Teimuraz Bandzava, San Jose, CA (US); Jinghan Ye, Cupertino, CA (US); Satrajit Misra, Cupertino, CA (US)

(73) Assignee: Koninklijke Philips N.V., Eindhoven (NL)

( * ) Notice: Subject to any disclaimer, the term of this patent is extended or adjusted under 35 U.S.C. 154(b) by 279 days.

(21) Appl. No.: 13/817,148

(22) PCT Filed: Jul. 18, 2011

(86) PCT No.: PCT/IB2011/053193
§ 371 (c)(1),
(2), (4) Date: Feb. 15, 2013

(87) PCT Pub. No.: WO2012/025842
PCT Pub. Date: Mar. 1, 2012

(65) Prior Publication Data
US 2013/0142410 A1    Jun. 6, 2013

Related U.S. Application Data

(60) Provisional application No. 61/376,871, filed on Aug. 25, 2010.

(51) Int. Cl.
*G06K 9/00* (2006.01)
*A61B 6/00* (2006.01)
(Continued)

(52) U.S. Cl.
CPC .............. *A61B 6/5288* (2013.01); *G06T 11/005* (2013.01); *G06T 2211/412* (2013.01); *G06T 7/2053* (2013.01); *G06T 2207/10108* (2013.01);
(Continued)

(58) Field of Classification Search
None
See application file for complete search history.

(56) References Cited

U.S. PATENT DOCUMENTS 5,381,791 A    1/1995    Qian
5,682,887 A    11/1997   Xu et al.
(Continued)

FOREIGN PATENT DOCUMENTS

WO    9318470 A1    9/1993
WO    9425879 A1    11/1994

OTHER PUBLICATIONS

Germano, G., et al.; Operator-less Processing of Myocardial Perfusion SPECT Studies; 1995; J. Nucl. Med.; 36(11)2127-2132.
(Continued)

*Primary Examiner* — Tahmina Ansari (57) ABSTRACT

An apparatus comprises: an imaging system (10) configured to acquire emission data from a cyclically varying element; a monitoring instrument (20, 22) configured to measure the cyclical varying of the cyclically varying element; and an electronic device (40) configured to locate an image feature corresponding to the cyclically varying element in the acquired emission data based on correlation of time variation of the emission data with the cyclical varying of the cyclically varying element measured by the monitoring instrument. The located image feature may be verified by: thresholding a projection image generated from the emission data to generate a mask image; identifying in the mask image one of (i) a hollow circular feature, (ii) a hollow oval feature, (iii) a circular cavity feature, and (iv) an oval cavity feature; and verifying the located image feature based on whether the identifying operation is successful.

22 Claims, 7 Drawing Sheets

(51) Int. Cl.
*G06T 11/00* (2006.01)
*G06T 7/20* (2006.01)
*A61B 5/0402* (2006.01)
*A61B 6/03* (2006.01)
*G06K 9/46* (2006.01)

(52) U.S. Cl.
CPC ..... *G06T 2207/30048* (2013.01); *A61B 5/0402* (2013.01); *A61B 6/037* (2013.01); *A61B 6/503* (2013.01); *A61B 6/5264* (2013.01); *G06K 9/46* (2013.01)

(56) References Cited

U.S. PATENT DOCUMENTS

| | | | |
|---|---|---|---|
| 6,065,475 A | 5/2000 | Qian et al. | |
| 6,535,623 B1 | 3/2003 | Tannenbaum et al. | |
| 6,757,414 B1 | 6/2004 | Turek et al. | |
| 7,623,709 B2 | 11/2009 | Gering | |
| 7,630,528 B2 * | 12/2009 | Kohler et al. | 382/128 |
| 7,683,331 B2 | 3/2010 | Chang | |
| 8,811,700 B2 * | 8/2014 | Wang et al. | 382/128 |
| 2007/0183639 A1 * | 8/2007 | Kohler et al. | 382/131 |
| 2008/0272304 A1 * | 11/2008 | Vija | 250/369 |
| 2009/0076369 A1 * | 3/2009 | Mistretta | 600/407 |
| 2012/0321153 A1 * | 12/2012 | Dwivedi et al. | 382/128 |
| 2013/0142410 A1 * | 6/2013 | Dwivedi et al. | 382/131 |
| 2014/0355858 A1 * | 12/2014 | O'Dell | 382/131 |

OTHER PUBLICATIONS

Lindenau, J., et al.; Spatial Reconstruction of the Opacified Myocardium from a Small Number of Projections; 1985; IEEE Trans. on Computers in Cardiology; pp. 351-354.

* cited by examiner

HEART LOCATION AND VERIFICATION IN EMISSION IMAGES

CROSS REFERENCE TO RELATED APPLICATIONS

This application is a national filing of PCT application Serial No. PCT/IB2011/053193, filed Jul. 18, 2011, published as WO 2012/025842 A2 on Mar. 1, 2012, which claims the benefit of U.S. provisional application Ser. No. 61/376,871 filed Aug. 25, 2010 which is incorporated herein by reference.

The following relates to the emission imaging arts, cardiac imaging arts, medical arts, image processing arts, and related arts.

In emission imaging, such as single photon emission computed tomography (SPECT) or positron emission tomography (PET), a subject such as a human medical patient or an animal veterinary patient, is administered a radiopharmaceutical including a radioisotope that emits detectable radiation. The radiopharmaceutical is selected or designed to concentrate in an organ or tissue of interest. Radiation detector arranged around and/or moving around the subject measure the detectable radiation emitted by the radioisotope and these measured data are reconstructed to form an emission image or map of the radiopharmaceutical distribution in the subject. A known emission imaging application is cardiac imaging, in which the radiopharmaceutical is selected or designed to concentrate in the cardiac organ or in the blood. The emission image or map therefore images the heart or blood in chambers (e.g., atria and/or ventricles) of the heart. In some applications, images may be acquired over a period of time in order to characterize the influx and washout of the radiopharmaceutical (or blood carrying the radiopharmaceutical) into and out of the heart.

One difficulty with cardiac emission imaging is the radiopharmaceutical may also tend to concentrate in other organs, especially the kidneys and liver. This creates multiple "hot spots" in the emission image, making it difficult to unambiguously ascertain which image feature or features correspond to the heart.

A known approach for locating the heart in an emission image is by the use of a complementary "anatomical" image such as a transmission computed tomography (CT) image. The anatomical image is spatially registered with the emission image and is then used to locate the heart. This approach has the disadvantages of requiring availability of a second imaging modality (e.g., CT) and reliance upon accurate image registration.

Another known approach is to utilize the emission image alone to locate the heart. Such approaches can be manual (e.g., the image is displayed via a graphical user interface and the user delineates the heart using a mouse pointer or other device) or automatic. Manual approaches can be tedious, while existing automated approaches can sometimes misidentify as the heart another organ in which the radiopharmaceutical concentrates, such as the liver or kidneys. In either manual or automatic heart location, the impact of the beating heart can be problematic, since this introduces a time variation in the data. Emission data collection is usually of order minutes to tens of minutes due to safety constraints on the maximum permissible radiopharmaceutical dose and consequently low emission event count rates.

One way to address this is to employ "summed" data, in which the heart beating is ignored and the resulting image is blurred. Nonetheless, the heart can usually be located in the blurred image. Alternatively, cardiac gating can be used based on an electrocardiograph (ECG) or other signal indicative of cardiac cycling. Here, only emission data collected in a narrow cardiac phase window is used for the image reconstruction and heart location processing. The result is less blurring, but at the cost of a substantial reduction in emission data for use in the image reconstruction and heart location processing. (By way of example, if the emission data are binned into eight cardiac phases yielding a coarse phase resolution, only about one-eighth of the emission data are used for locating the heart).

After the heart is located, it is advantageous to verify accuracy of the heart delineation. Such verification provides a check to ensure that the liver, a kidney, or some other feature is not misidentified as the heart, and also preferably provides more precise delineation of the heart in the emission image.

The following provides new and improved apparatuses and methods as disclosed herein.

In accordance with one disclosed aspect, a method comprises: binning emission data acquired from a cyclically varying element into a plurality of different phases of the cyclical varying; computing difference emission data comprising differences between emission data in the different phases of the cyclical varying; and locating an image feature corresponding to the cyclically varying element in the emission data based on the difference emission data; wherein at least the computing and locating are performed by an electronic device.

In accordance with another disclosed aspect, a method comprises: reconstructing emission data acquired from a cyclically varying element to generate a reconstructed image; locating an image feature corresponding to the cyclically varying element in the emission data acquired from the cyclically varying element; thresholding a projection image generated from the emission data to generate a mask image; identifying in the mask image one of (i) a hollow circular feature, (ii) a hollow oval feature, (iii) a circular cavity feature, and (iv) an oval cavity feature; and verifying the located image feature based on whether the identifying operation is successful; wherein at least the computing and locating are performed by an electronic device.

In accordance with another disclosed aspect, a digital processor is configured to perform a method as set forth in any one of the two immediately preceding paragraphs. In accordance with another disclosed aspect, a storage medium is disclosed storing instructions executable on a digital processor to perform a method as set forth in any one of the two immediately preceding paragraphs.

In accordance with another disclosed aspect, an apparatus comprises: an imaging system configured to acquire emission data from a cyclically varying element; a monitoring instrument configured to measure the cyclical varying of the cyclically varying element; and an electronic device configured to locate an image feature corresponding to the cyclically varying element in the acquired emission data based on correlation of time variation of the emission data with the cyclical varying of the cyclically varying element measured by the monitoring instrument.

One advantage resides in more efficient location of a heart or other cyclically varying element in an emission image.

Another advantage resides in more reliable verification of a localized heart or other localized feature.

Further advantages will be apparent to those of ordinary skill in the art upon reading and understanding the following detailed description.

Figure 1:
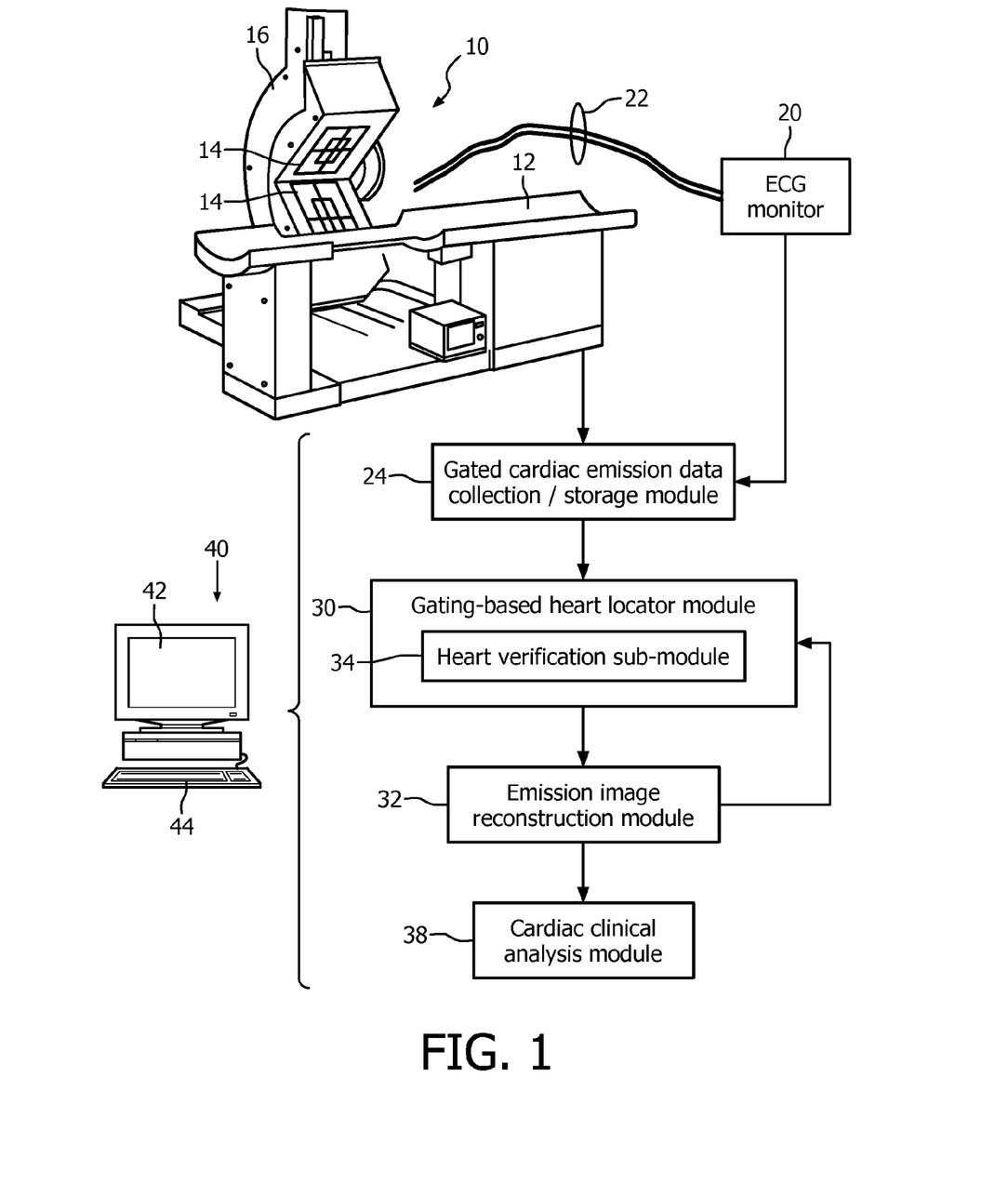
FIG. 1 diagrammatically shows a cardiac SPECT imaging system including heart location and verification.

With reference to FIG. 1, an imaging system 10 includes an imaging apparatus for acquiring an emission image. The illustrative imaging system 10 is a CardioMD™ gamma camera (available from Koninklijke Philips Electronics N.V., Eindhoven, The Netherlands) configured to acquire cardiac SPECT data of a subject lying on a subject support 12 using radiation detectors 14 mounted on a C-arm 16. In other embodiments, another type of imaging system may be used to acquire emission data. By way of another example, the imaging system may be a GEMINI™ imaging system (available from Koninklijke Philips Electronics N.V., Eindhoven, The Netherlands) configured to acquire PET imaging data. SPECT, PET, or other emission data are acquired over a sufficiently large span of angular views, such as a 180° or 360° span of views, by moving the radiation detectors 14 around the subject and/or by providing a ring or arc of radiation detectors of the requisite angular span. A suitable radiopharmaceutical is typically administered to the subject (not shown) by intravenous injection, ingestion, inhalation, or another input pathway prior to acquisition of emission data. A time delay may be interposed between administering the radiopharmaceutical and acquiring the emission data to provide time for the radiopharmaceutical to collect in the heart or other organ of interest. In the illustrative examples herein, the organ of interest is the heart, but it is also contemplated for the organ of interest to be the lungs or another cyclically moving organ or tissue, or an organ or tissue that does not cyclically move.

In some embodiments in which the organ or tissue of interest moves cyclically, an instrument is provided to monitor the cyclical motion. In the illustrative examples the cyclical motion is the beating of the heart (i.e., cardiac cycling), and an electrocardiographic (ECG) monitor 20 is provided to monitor the cardiac cycling. Suitable electrodes or leads 22 operatively connect the ECG monitor 20 with the subject in order to acquire a chosen ECG signal (e.g., using a standard 12-lead ECG configuration, or a simplified 4-lead ECG configuration, or so forth). A gated cardiac emission data collection/storage module 24 collects emission data acquired by the imaging system 10 and stores the emission data in cardiac phase bins based on the cardiac cycling information provided by the ECG monitor 20. For example, in one approach, N equal-sized cardiac phase bins are used, each cardiac phase bin having a size of T/N in units of seconds where T denotes the duration of a single heart beat in units of seconds. Bins of unequal size are also contemplated, for example in order to provide relatively higher temporal resolution for more dynamic portions of the cardiac cycle and relatively lower temporal resolution for more quiescent portions of the cardiac cycle.

With continuing reference to FIG. 1, a gating-based heart locator module 30 processes the gated cardiac emission data to locate the heart in the emission data. In some embodiments, the heart locating process identifies the heart by automatically identifying emission data that varies over time in correspondence with the cardiac cycling, for example by computing differences or derivatives between emission data in different cardiac phase bins. Such differences or derivatives may be computed in projection space, with difference or differential projection data being reconstructed by an emission image reconstruction module 32. Alternatively, the differences or derivatives may be computed in image space after reconstruction of the emission data of each cardiac phase bin by the reconstruction module 32. An optional heart verification sub-module 34 of the locator module 32 optionally performs heart verification and/or refinement of the heart delineation.

The emission data, or a portion thereof identified by the heart locator 30 as being emitted from the heart, are reconstructed by the reconstruction module 32 to generate a cardiac image (or a series of cardiac images, for example in the case of a radiopharmaceutical uptake and/or washout study). In some embodiments the entire (summed) dataset is reconstructed, while in other embodiments only data from a selected phase bin or bins is reconstructed. The cardiac image or images are optionally processed by a post-processing system such as an illustrative cardiac clinical analysis module 38 which performs analyses to generate quantitative or qualitative clinical information for review and/or use by a cardiologist or other medical personnel.

The various processing components or modules 24, 30, 32, 34, 38 are suitably embodied by an illustrative computer 40 or another electronic device including a digital processor (for example, a digital microprocessor, a digital microcontroller, a digital graphical processing unit, or so forth) and optionally also incorporating analog and/or digital application-specific integrated circuitry (ASIC) or other hardware. A display 42 of the computer 40, or some other display and/or printing device, is suitably used to display the emission images or portions thereof and/or images derived therefrom. The computer 40 or other electronic device also suitably includes an illustrative keyboard 44, or a mouse, trackball, trackpad, or other user input device by which a radiologist or other medical personnel operates the imaging system 10 including the various processing components or modules 24, 30, 32, 34, 38.

Moreover, the various processing components or modules 24, 30, 32, 34, 38 may additionally or alternatively be embodied as a storage medium storing instructions executable by the illustrated computer 40 or other electronic device to perform the disclosed emission data processing methods. The storage medium may, by way of illustrative example, include a hard drive or other magnetically-based storage medium, an optical disk or other optically-based storage medium, a random access memory (RAM), read-only memory (ROM), FLASH memory, or other electronic storage medium, or so forth, or various combinations thereof.

Figure 2:
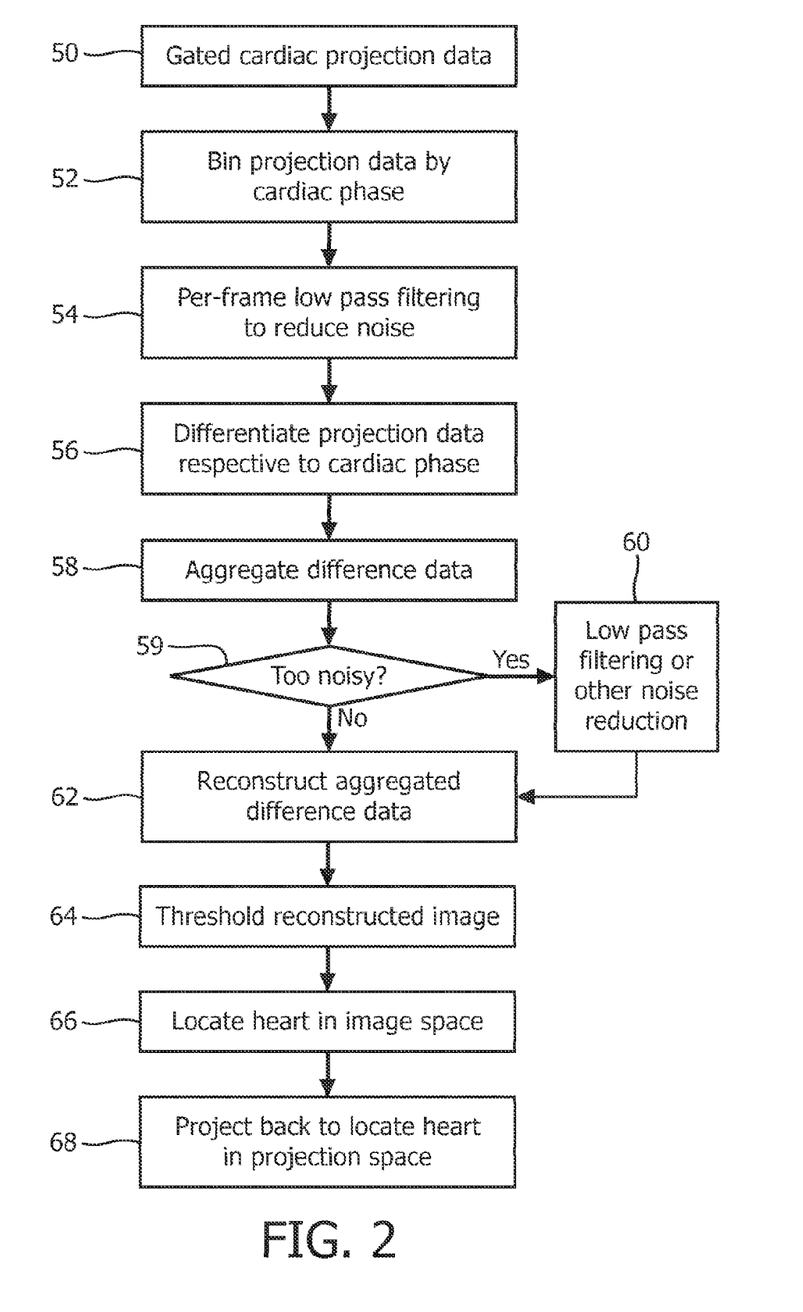
FIG. 2 diagrammatically shows heart location in an emission image suitably performed by the system of FIG. 1.

With reference to FIG. 1 and with further reference to FIG. 2, some suitable gating-based heart locating approaches suitably performed by the heart locator module 30 are described. To initiate, gated cardiac projection data 50 are loaded and are binned by cardiac phase in an operation 52. For example, the operation 52 may be performed by the collection/storage module 24 which in one approach bins the projection data into N equal-sized cardiac phase bins each having a bin size of T/N in units of seconds where T denotes the duration of a single heart beat in units of seconds. Again, bins of unequal sizes are also contemplated. If unequal bin sizes are employed, then the operation 52 optionally compensates for the differences in acquisition time interval by scaling with appropriate factors for each gating bin. In an optional operation 54, optional low-pass filtering is applied frame-by-frame to smooth the projections and reduce noise. The projection data are then differentiated between gating phases in an operation 56. In one approach, difference emission data comprising differences between emission data in the different phases of the cyclical varying are computed in the operation 56. For example, if there are 8 cardiac phase bins, one approach for computing difference emission data is to take the difference between projection data in cardiac phase bins 1 and 5, and between projection data in cardiac phase bins 2 and 6, and between projection data in cardiac phase bins 3 and 7, and between projection data in cardiac phase bins 4 and 8. Difference projection data are computed for each projection viewing angle. In an operation 58, the difference projection data from the operation 56 are averaged for each projection viewing angle. Since the cardiac phase bins correlated with cardiac phases, the heart is expected to be the dominant object in the averaged difference data, while other organs or background should have lower signal intensity as compared with the heart. Optionally, another noise reduction process may be performed after the differential operations 56, 58. In the illustrative example of FIG. 2, this optional noise reduction is performed as follows. A decision operation 59 decides whether the additional noise reduction processing is appropriate (that is, decides if the difference data are too noisy). If so, then an additional low pass filtering or other noise reduction operation 60 is performed.

To locate the heart in image space, the aggregated difference data are reconstructed in an operation 62, the resulting aggregated difference image is thresholded or otherwise processed in an operation 64 to isolate the heart in the image, and the heart is located in an operation 66. In one suitable approach, the reconstruction operation 62 performs a quick reconstruction of the averaged difference data into the volume image domain without any correction (although applying correction is also contemplated). In the operation 64, a typical threshold is expected to be about 35% of the maximum value, although the optimal threshold may be different depending upon imaging conditions, signal to noise ratios (SNR), and other factors. The operation 64 removes background signal so that the heart is more definitively delineated. The locating operation 66 in one approach includes locating the heart in the volume image domain by calculating the mass centroid in the image after the processing 64. The locating operation 66 optionally may also apply a local-region mass centroid calculation again for finer tune up search. Other approaches such as segmentation or region-growing approaches may also be used in the locating operation 66. If the location of the heart in the projection space or domain is desired, then in an operation 68 the heart location identified in image space is suitably projected back into the projection domain to obtain the heart location for each frame.

The illustrative processing sequence of FIG. 2 performs the differentiation 56, 58 in projection space, and then reconstructs the difference projection data in the operation 62 to locate the heart in image space. Alternatively, the projection data for each cardiac phase bin may be first reconstructed to generate a set of images for the different cardiac phases, and the differentiation may be performed in image space (for example, in the example of 8 cardiac phase bins, computing: differences between the two images reconstructed from cardiac phase bins 1 and 5, and differences between the two images reconstructed from cardiac phase bins 2 and 6, and differences between the two images reconstructed from cardiac phase bins 3 and 7, and differences between the two images reconstructed from cardiac phase bins 4 and 8, and then aggregating the computed difference images analogous to the operation 58. In either case, the aggregating can employ averaging, summing, or another aggregation operation.

Figure 3:
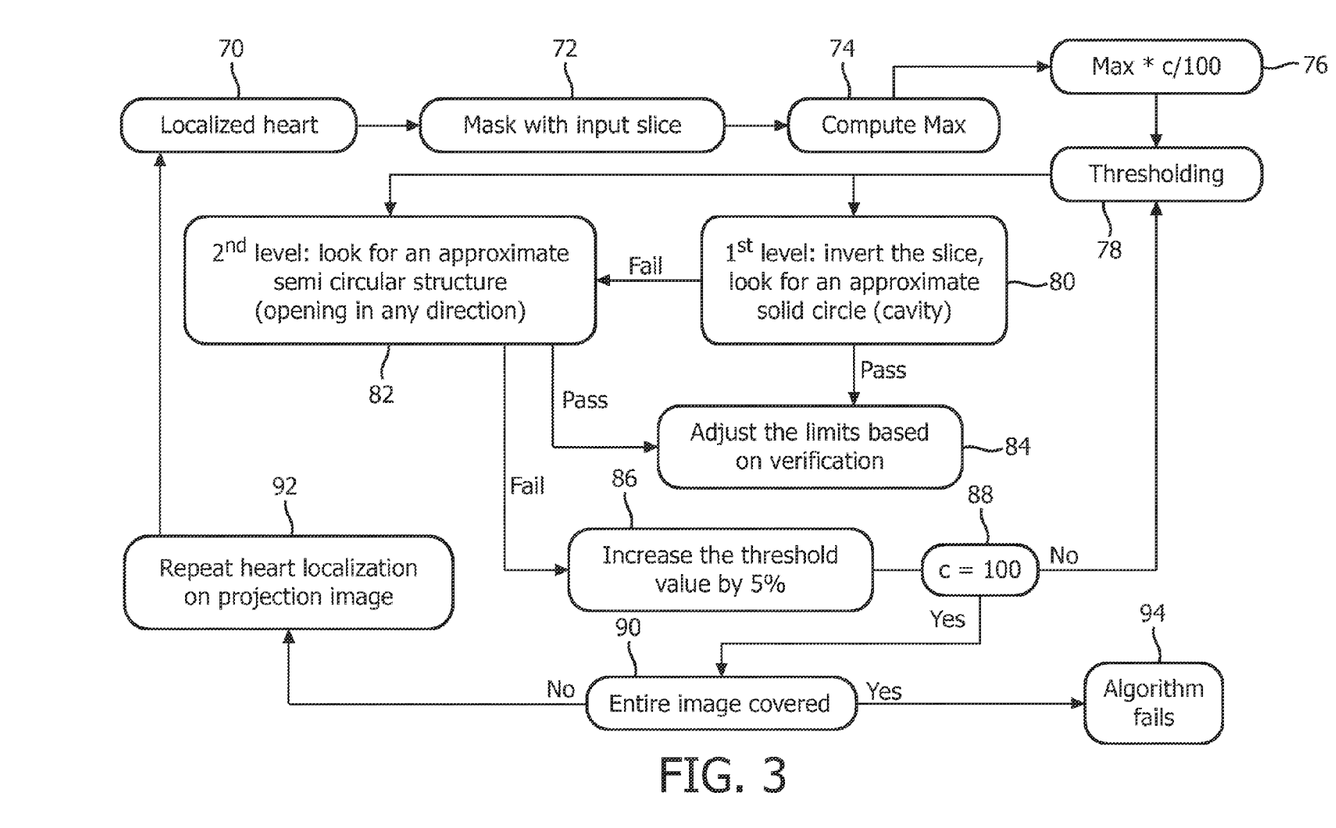
FIG. 3 diagrammatically shows verification and refinement of the heart location in an emission image suitably performed by the system of FIG. 1.

With reference to FIG. 1 and with further reference to FIG. 3-9, some suitable heart verification approaches suitably performed by the heart verification sub-module 34 are described. The heart verification operates on a projection image generated from the emission data. FIG. 3 diagrams an overall illustrative heart verification process. Not shown in FIG. 3 is optional noise filtering optionally performed prior to entering the heart shape detection routine diagrammed in FIG. 3. The verification processing of FIG. 3 suitably starts with a (proposed) localized heart 70, for example output by the heart locating procedure described herein with reference to FIG. 2. A masking operation 72 isolates the (proposed) localized heart for verification processing, and an operation 74 computes an initial threshold 76 that is applied in a thresholding operation 78 to generate a binary mask or binary image representation of the (proposed) localized heart.

The heart verification process of FIG. 3 employs a shape-based verification process, which is based on the expected shape and size of the heart. For example, the heart typically appears as an open circle or partial open circle in emission images (e.g., SPECT or PET images). In view of this, the heart verification process of FIG. 3 includes a first-level shape analysis operation 80 that compares the (proposed) localized heart with the open circle configuration, and a second-level shape analysis operation 82 that compares the (proposed) localized heart with the partial open circle configuration.

If either shape analysis 80, 82 is passed, then processing flows to an optional adjustment operation 84 that adjusts the (proposed, and now verified) localized heart based on the verification results. The optional adjustment entails providing a more precise delineation of the heart location based on the shape analysis.

If both the first shape analysis 80 and the second shape analysis 82 fail, this does not (at least in the first pass) necessarily mean that the proposed localized heart has failed the verification. Rather, it could mean that the threshold 76 used in the verification shape analyses should be adjusted. Toward this end, an operation 86 increases the threshold by a selected amount (e.g., 5% in illustrative FIG. 3). In an operation 88 it is determined whether the updated threshold is in a usable range (e.g., less than 100 in the illustrative example) and if so process flow returns to the thresholding operation 78 to repeat the thresholding using the updated threshold and repeat the shape analyses 80, 82.

If the operation 88 indicates that the full usable range of thresholds has been employed and the shape analyses 80, 82 have failed for all thresholds, then process flow moves to an operation 90 at which it is determined whether any other region of the image is a proposed localized heart. If so, then in an operation 92 the next proposed localized heart is chosen as the proposed localized heart 70 and the process repeats. On the other hand, if the operation 90 determines that no region of the image remains to be tested as a proposed localized heart, then process flows to a heart verification failure operation 94 that reports heart verification failure and/or takes other remedial action.

Figure 4:
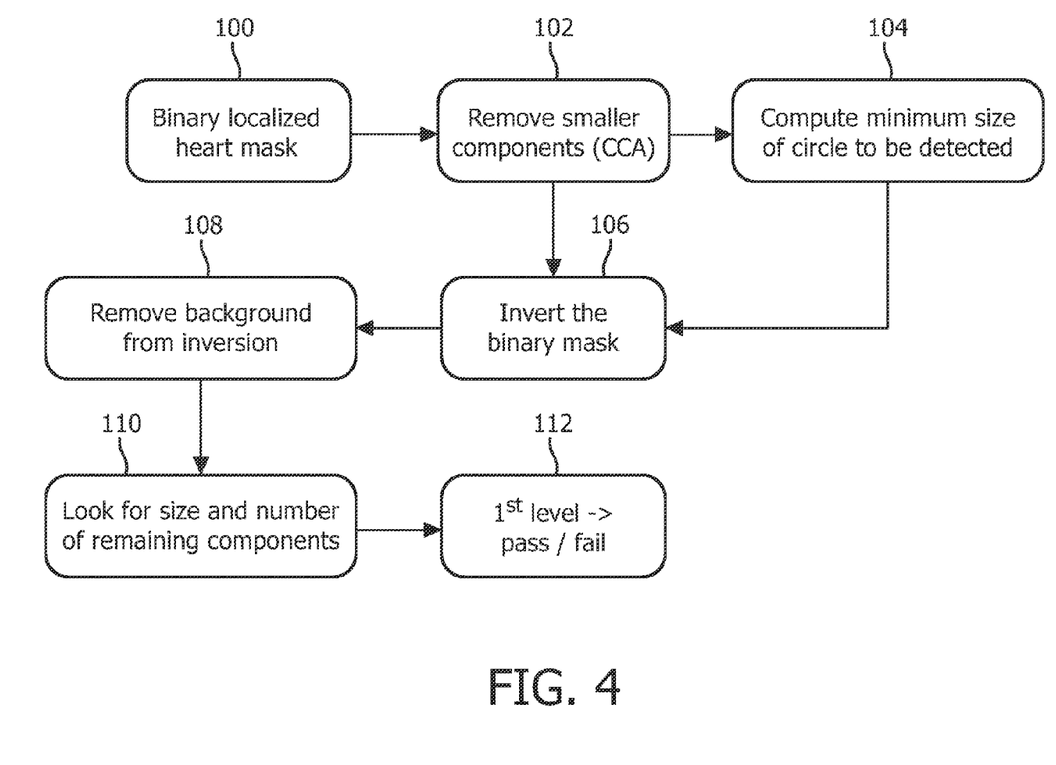
FIGS. 4-6 diagrammatically shows a sub-process for verifying a substantially round or oval located heart feature.
Figure 5:
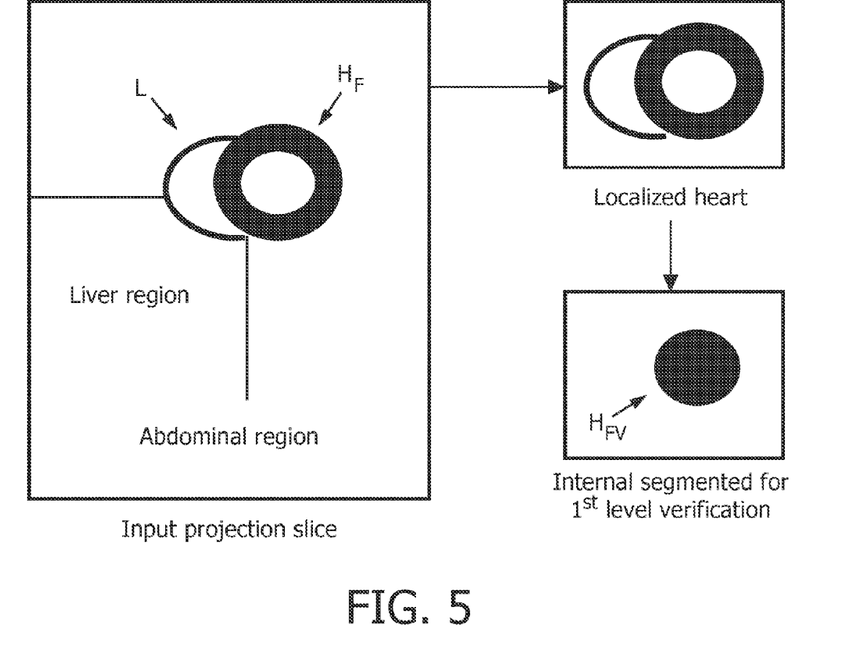
Figure 6:
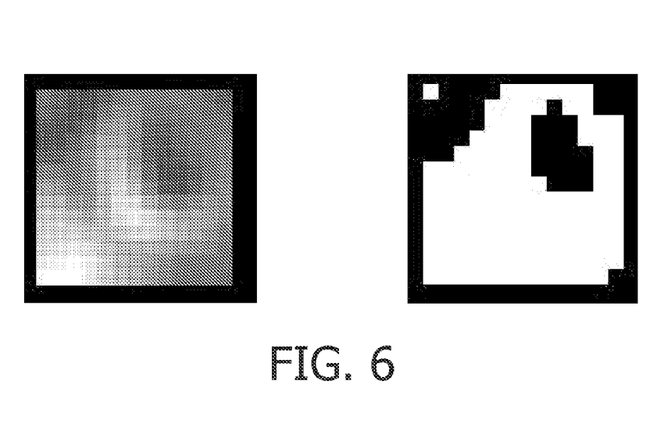

With continuing reference to FIG. 3 and with further reference to FIGS. 4-6, some suitable approaches for performing the first-level shape analysis operation 80 that compares the (proposed) localized heart with the open circle configuration are described. FIG. 5 is first considered, which diagrammatically shows the typical feature configuration in the image. The left side of FIG. 5 diagrammatically shows a typical input projection, in which the heart is imaged as an open circle $H_F$, and is obscured by secondary features such as a liver feature L. The upper right of FIG. 5 shows the (proposed) localized heart such as may be identified by way of illustrative example by the processing of FIG. 2. The lower right of FIG. 5 shows the binary mask created by the thresholding operation 78 (see FIG. 3) and processing by the first-level shape analysis operation 80 including noise filtering and inversion of the binary mask. A simply-connected solid circular feature $H_{FV}$ shown in the lower right of FIG. 5 represents the verified heart.

With particular reference to FIG. 4, suitable processing performed by the first-level shape analysis operation 80 is described. The processing operates on the binary localized heart mask 100 output by the thresholding operation 78 (see FIG. 3). A noise-filtering operation 102 is performed to remove smaller components that are too small to be the heart. In a suitable approach the noise filtering operation 102 employs fully connected image based connected component analysis (CCA) in 2D. Based on the features remaining after the CCA, an operation 104 computes the minimum size of circle to be detected. An operation 106 performs a binary mask inversion. In this operation the "on" or black pixels are switched to "off" or white pixels, and vice versa). This converts the shape analysis to detection of a simply-connected filled circular feature. An additional noise filtering operation 108 is optionally performed to remove background noise from the inverted binary mask. In an operation 110, a search for a suitably sized solid circular object is performed in the inverted (and optionally noise-filtered) binary mask. An operation 112 reports success or failure of the first-level shape analysis operation 80. If success is reported, then the best-fit filled circular feature $H_{FV}$ is optionally also reported for use in the optional adjustment operation 84 (see FIG. 3). In one approach, the size of the circle is derived from the number of non-zero pixels in the binary mask.

FIG. 6 provides an illustration of a successfully performed instance of the first-level shape analysis operation 80 (that is, an instance that verifies a proposed localized heart. The left side of FIG. 6 shows a proposed localized heart in gray scale image (that is, before any thresholding). The right side of FIG. 6 shows the binary mask output from the first-level shape analysis operation 80.

Figure 7:
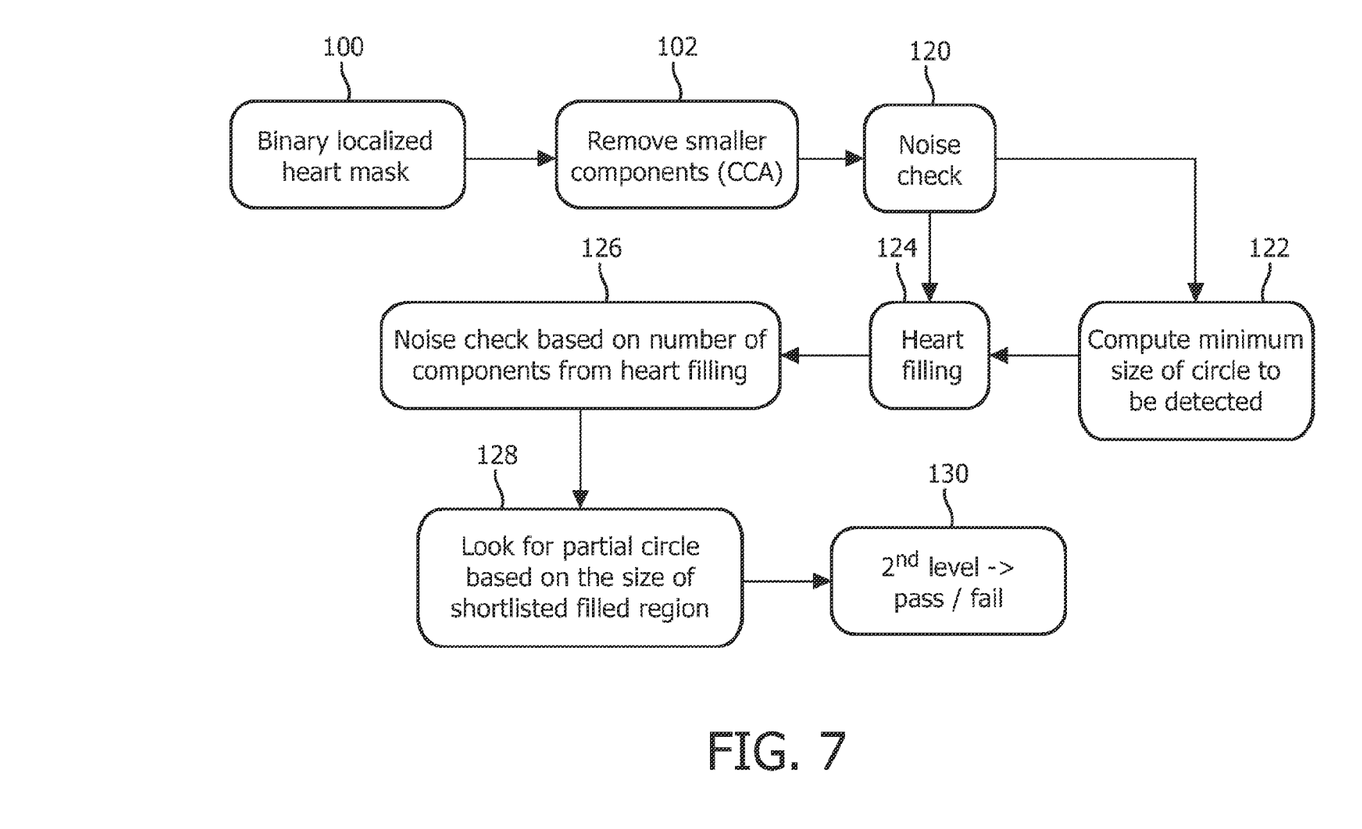
FIGS. 7-9 diagrammatically shows a sub-process for verifying a substantially indented or crescent-shaped located heart feature.
Figure 8:
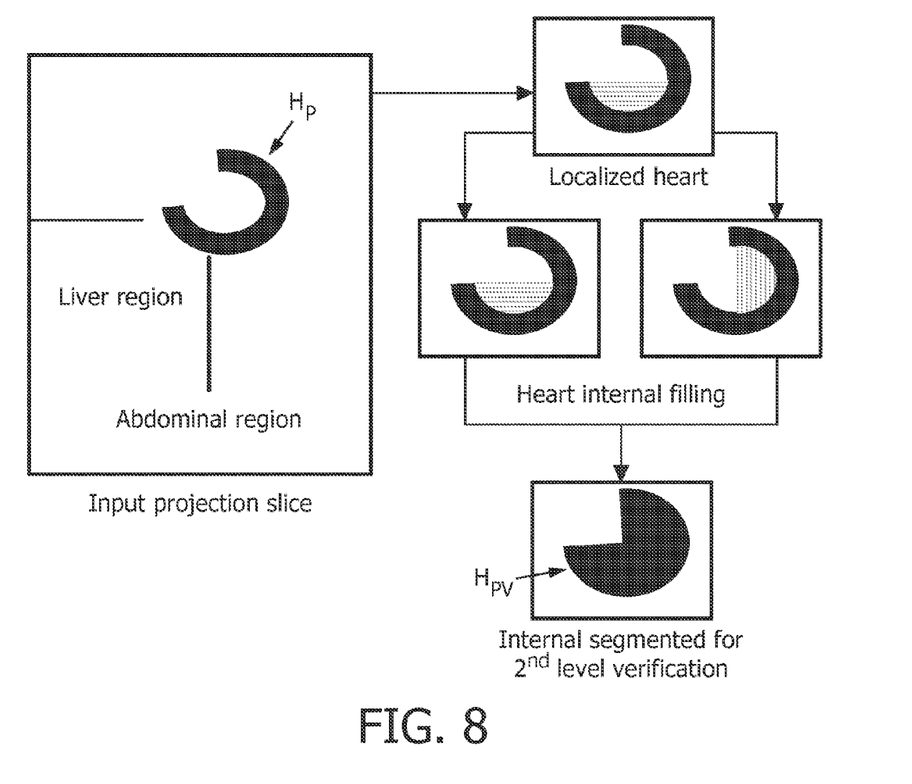
Figure 9:
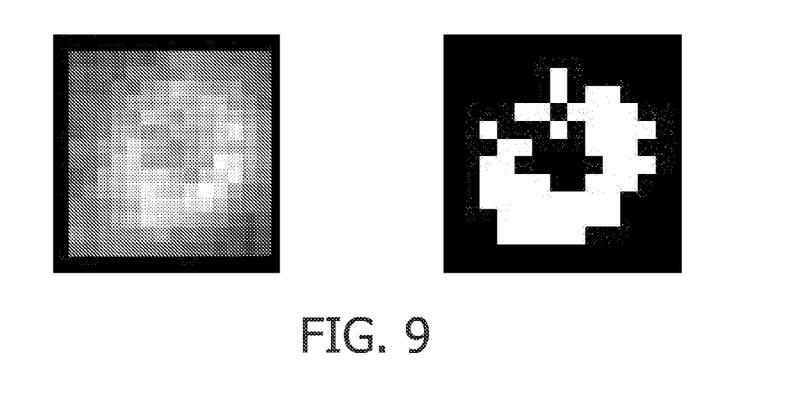

With continuing reference to FIG. 3 and with further reference to FIGS. 7-9, some suitable approaches for performing the second-level shape analysis operation 82 that compares the (proposed) localized heart with the open partial circle configuration are described. FIG. 8 is first considered, which diagrammatically shows the typical feature configuration in the image. The left side of FIG. 8 diagrammatically shows a typical input projection, in which the heart is imaged as an partial open circle H. The upper right of FIG. 8 shows the (proposed) localized heart such as may be identified by way of illustrative example by the processing of FIG. 2. The lower right of FIG. 8 shows the binary mask created by the thresholding operation 78 (see FIG. 3) and processing by the second-level shape analysis operation 82 including filling of the inside of the partial open circle H. The filling generates a simply-connected solid partial circular feature $H_{PV}$ (shown in the lower right of FIG. 8) that represents the verified heart.

With particular reference to FIG. 7, suitable processing performed by the second-level shape analysis operation 82 is described. The processing again operates on the binary localized heart mask 100 output by the thresholding operation 78 (see FIG. 3). The noise-filtering operation 102 is again performed to remove smaller components that are too small to be the heart. In a suitable approach the noise filtering operation 102 employs fully connected image based connected component analysis (CCA) in 2D and face connected CCA is employed to detect noise. To enhance efficiency, the noise filtering operation 102 may optionally be performed only once and the output stored and used in both first and second shape analysis operations 80, 82.

A noise check is performed in an operation 120. If noise is present (even after the CCA) then there will be significantly higher number of face connected components as compared to fully connected component. If noise remains after the operation 102, the number of shortlisted regions to verify as heart (circular cavity or partial circular cavity) should not be significantly higher as compared to the size of the binary mask. If it is noise, this number will be comparatively higher than normal heart region, and this information is exploited in noise removal.

Based on the features remaining after the CCA, an operation 122 computes the minimum size of the partial circle to be detected. An operation 124 performs heart filling as diagrammatically depicted in FIG. 8. The heart filling operation 124 fills the extant portion of the partial open circle to produce a simply-connected segmented region $H_{PV}$ corresponding to a portion (e.g., three-quarters) of a filled circle, as shown in the bottom right of FIG. 8. An additional noise filtering operation 126 is optionally performed to remove background noise after the heart filling 124. In an operation 126, the verified heart is identified based on the partial filled circle feature $H_{PV}$. An operation 130 reports success or failure of the second-level shape analysis operation 82. If success is reported, then the best-fit partial filled circular feature $H_{PV}$ is optionally also reported for use in the optional adjustment operation 84 (see FIG. 3).

FIG. 9 provides an illustration of a successfully performed instance of the second-level shape analysis operation 80 (that is, an instance that verifies a proposed localized heart. The left side of FIG. 9 shows a proposed localized heart in gray scale image (that is, before any thresholding). The right side of FIG. 9 shows the binary mask output from the second-level shape analysis operation 82.

In the verification process is described in FIGS. 3-9 with reference to verification of a proposed localized heart, the mentioned circular features may more generally be oval features. Although the verification process is described in FIGS. 3-9 with reference to verification of a proposed localized heart, it will be appreciated that the process can also be applied to the verification of other features of interest in an emission image, such as a left or right lung.

The locating approach described for a heart with reference to FIG. 2 is applicable to locating another cyclically varying element in emission data. For example, the cyclically varying element may be a major blood vessel that does not physically move but which has cyclically varying emission output in correspondence with blood flow through the blood vessel.

This application has described one or more preferred embodiments. Modifications and alterations may occur to others upon reading and understanding the preceding detailed description. It is intended that the application be construed as including all such modifications and alterations insofar as they come within the scope of the appended claims or the equivalents thereof.

Having thus described the preferred embodiments, the invention is now claimed to be:

1. A method comprising:
   binning emission projection data acquired from a cyclically varying element into a plurality of different phases of the cyclical varying;
   computing pairwise difference emission projection data in projection data space comprising differences between emission projection data in different pairs of phases of the cyclical varying;
   aggregating the pairwise difference emission projection data computed for the different pairs of phases of the cyclical varying to generate difference emission projection data; and locating an image feature corresponding to the cyclically varying element in the emission projection data based on the difference emission projection data;

wherein at least the computing and locating are performed by an electronic device.

2. The method as set forth in claim 1, wherein the cyclically varying element is a beating heart, the cyclical varying is the beating of the heart, and the plurality of different phases are a plurality of different cardiac phases of the beating of the heart.

3. The method as set forth in claim 1, wherein the locating comprises:

reconstructing the difference emission projection data to generate a locator image; and locating the cyclically varying element in the locator image by operations including at least one of (i) thresholding the locator image, (ii) calculating a mass centroid in the locator image, (iii) performing segmentation of the locator image, and (iv) performing region growing in the locator image.

4. The method as set forth in claim 1, wherein the locating comprises:

reconstructing the difference emission projection data to generate a locator image; and locating the cyclically varying element in the locator image.

5. The method as set forth in claim 4, wherein the locating further comprises:

backprojecting the locator image to generate locator projection data; and locating the image feature corresponding to the cyclically varying element in the locator projection data.

6. The method as set forth in claim 1, further comprising:

reducing noise in the emission data acquired from the cyclically varying element by low-pass filtering the emission data acquired from the cyclically varying element.

7. The method as set forth in claim 1, further comprising:

verifying the located image feature corresponding to the cyclically varying element by a verification process including:

thresholding a projection image generated from the emission data to generate a mask image, identifying in the mask image one of (i) a hollow circular feature, (ii) a hollow oval feature, (iii) a circular cavity feature, and (iv) an oval cavity feature, and verifying the located image feature based on whether the identifying operation is successful.

8. The method as set forth in claim 7, wherein the identifying operation of the verification process includes:

inverting the mask image; and identifying in the mask image one of (i) a filled circular feature, (ii) a filled oval feature, (iii) a partially filled circular feature, and (iv) a partially filled oval feature.

9. The method as set forth in claim 7, wherein the verification process includes performing a plurality of iterations of the thresholding and identifying operations with an increased threshold used in the thresholding in each successive iteration.

10. The method as set forth in claim 7, wherein the verification process is performed on a region of the projection image that is (i) smaller than the entire projection mage and (ii) defined by the located image feature corresponding to the cyclically varying element.

11. A method comprising:

reconstructing emission data acquired from a cyclically varying element to generate a reconstructed image;

locating an image feature corresponding to the cyclically varying element in the emission data acquired from the cyclically varying element;

thresholding a projection image generated from the emission data to generate a mask image;

identifying in the mask image one of (i) a hollow circular feature, (ii) a hollow oval feature, (iii) a circular cavity feature, and (iv) an oval cavity feature; and verifying the located image feature based on whether the identifying operation is successful;

wherein at least the computing and locating are performed by an electronic device.

12. The method as set forth in claim 11, wherein the cyclically varying element is a beating heart.

13. The method as set forth in claim 11, further comprising:

after the thresholding and prior to the identifying, reducing noise in the mask image by performing a connected component analysis (CCA) on the mask image.

14. The method as set forth in claim 11, wherein the identifying comprises:

inverting the mask image; and identifying in the mask image one of (i) a filled circular feature, (ii) a filled oval feature, (iii) a partially filled circular feature, and (iv) a partially filled oval feature.

15. The method as set forth in claim 11, further comprising performing a plurality of iterations of the thresholding and identifying operations with an increased threshold used in the thresholding in each successive iteration, the verifying being based on whether any iteration of the identifying operation is successful.

16. The method as set forth in claim 11, wherein the thresholding, identifying, and verifying operations are performed on a region of the projection image that is (i) smaller than the entire projection image and (ii) defined by the located image feature corresponding to the cyclically varying element.

17. A digital processor configured to perform a method as set forth in claim 1.

18. A non-transitory storage medium storing instructions that are executable on a digital processor to perform a method as set forth in claim 1.

19. An apparatus comprising: an imaging system configured to acquire emission data comprising projection data in projection space from a beating heart; an electrocardiographic (ECG) instrument configured to measure an electrocardiographic signal of the cyclical varying of the beating heart; and an electronic device configured to locate an image feature corresponding to the beating heart in the acquired emission data based on correlation of time variation of the emission data with the electrocardiographic signal measured by the ECG instrument by operations including: computing difference projection data in projection data space comprising differences between projection data acquired at different time intervals of the cyclical varying of the beating heart as measured by the ECG instrument, and locating the image feature corresponding to the beating heart based on the difference projection data.

20. The apparatus as set forth in claim 19, wherein the electronic device is configured to compute the difference projection data in projection data space comprising an aggregation of pairwise differences between projection data acquired for different pairs of phases of the cyclical varying of the beating heart as measured by the ECG instrument.

21. The apparatus as set forth in claim 19, wherein the electronic device is configured to locate the image feature corresponding to the beating heart by operations including:

reconstructing the difference projection data to generate a locator image; and thresholding the locator image to isolate the beating heart in the locator image.

22. The apparatus as set forth in claim 19, wherein the electronic device is configured to locate the image feature corresponding to the beating heart by operations including:
   reconstructing the difference projection data to generate a locator image; and
   performing segmentation or region growing on the locator image to locate the beating heart in the locator image.

\* \* \* \* \*